(12) United States Patent
Pimenta

(10) Patent No.: US 9,468,536 B1
(45) Date of Patent: Oct. 18, 2016

(54) SPINAL FUSION IMPLANTS AND RELATED METHODS

(71) Applicant: NuVasive, Inc., San Diego, CA (US)

(72) Inventor: Luiz Pimenta, Sao Paulo (BR)

(73) Assignee: NuVasive, Inc., San Diego, CA (US)

(*) Notice: Subject to any disclaimer, the term of this patent is extended or adjusted under 35 U.S.C. 154(b) by 0 days.

(21) Appl. No.: 13/668,209

(22) Filed: Nov. 2, 2012

Related U.S. Application Data

(60) Provisional application No. 61/554,875, filed on Nov. 2, 2011.

(51) Int. Cl.
A61F 2/44 (2006.01)

(52) U.S. Cl.
CPC .................. A61F 2/4455 (2013.01)

(58) Field of Classification Search
CPC ......... A61F 2/44; A61F 2/4455; A61F 2/447
USPC ..................... 606/246–249; 623/17.11–17.16
See application file for complete search history.

(56) References Cited

U.S. PATENT DOCUMENTS

| | | |
|---|---|---|
| 5,397,364 A | 3/1995 | Kozak |
| 5,522,899 A | 6/1996 | Michelson |
| 6,258,125 B1 | 7/2001 | Paul |
| 6,302,914 B1 | 10/2001 | Michelson |
| 6,468,311 B2 | 10/2002 | Boyd |
| 6,558,424 B2 | 5/2003 | Thalgott |
| 6,719,794 B2 | 4/2004 | Gerber |
| 6,723,126 B1 | 4/2004 | Berry |
| 6,726,720 B2 | 4/2004 | Ross |
| 6,743,256 B2 | 6/2004 | Mason |
| D493,533 S | 7/2004 | Blain |
| 6,761,738 B1 | 7/2004 | Boyd |
| 6,974,480 B2 | 12/2005 | Messerli |
| 7,011,685 B2 | 3/2006 | Arnin |
| 7,018,413 B2 | 3/2006 | Krueger |
| 7,018,416 B2 | 3/2006 | Hanson |
| 7,060,100 B2 | 6/2006 | Ferree |
| D530,423 S | 10/2006 | Miles |
| 7,214,243 B2 | 5/2007 | Taylor |
| 7,226,482 B2 | 6/2007 | Messerli |
| 7,267,690 B2 | 9/2007 | Felt |
| 7,288,115 B2 | 10/2007 | Hawkins |
| 7,323,011 B2 | 1/2008 | Shepard |
| 7,491,237 B2 | 2/2009 | Randall |
| D594,986 S | 6/2009 | Miles |
| D599,019 S | 8/2009 | Pimenta |
| 7,618,458 B2 | 11/2009 | Biedermann |
| D621,509 S | 8/2010 | Lovell |
| 7,780,732 B2 | 8/2010 | Abernathie |
| 7,850,734 B2 | 12/2010 | Oh |

(Continued)

FOREIGN PATENT DOCUMENTS

CN 201719408 1/2011
WO WO-02/065957 8/2002

Primary Examiner — Ellen C Hammond
Assistant Examiner — Christina Negrellirodrigue
(74) Attorney, Agent, or Firm — Jeremy A. Smith; Bradley Arant Boult Cummings LLP

(57) ABSTRACT

A system and methods for promoting fusion across an intervertebral disc space, the system including a system of spinal fusion implants including a distal implant, a proximal implant and a medial implant positioned therebetween, wherein the medial implant has a flexible anterior wall capable of being deformed when a force is exerted upon it.

6 Claims, 3 Drawing Sheets

(56) References Cited

U.S. PATENT DOCUMENTS

| | | |
|---|---|---|
| 8,002,833 B2 | 8/2011 | Fabris |
| 8,110,004 B2 | 2/2012 | Valdevit |
| 8,128,700 B2 | 3/2012 | Delurio |
| 8,163,026 B2 | 4/2012 | Gray |
| 8,187,329 B2 | 5/2012 | Theofilos |
| 8,241,359 B2 | 8/2012 | Davis |
| 8,273,127 B2 | 9/2012 | Jones |
| 8,287,572 B2 | 10/2012 | Bae |
| D671,645 S | 11/2012 | Curran et al. |
| D674,092 S | 1/2013 | Lovell |
| D675,320 S | 1/2013 | Oi |
| D696,402 S | 12/2013 | Oi |
| 8,617,244 B2 | 12/2013 | Reichen |
| 8,673,010 B2 | 3/2014 | Compton |
| 8,709,083 B2 | 4/2014 | Duffield |
| D708,747 S | 7/2014 | Curran |
| D711,537 S | 8/2014 | Pimenta |
| 8,900,307 B2 | 12/2014 | Hawkins |
| D721,808 S | 1/2015 | Oi |
| 2002/0183850 A1 | 12/2002 | Felt |
| 2003/0139812 A1 | 7/2003 | Garcia |
| 2004/0002758 A1 | 1/2004 | Landry |
| 2004/0010318 A1 | 1/2004 | Ferree |
| 2005/0107795 A1 | 5/2005 | Morris |
| 2005/0177245 A1 | 8/2005 | Leatherbury |
| 2006/0195191 A1 | 8/2006 | Sweeney |
| 2006/0235535 A1 | 10/2006 | Ferree |
| 2007/0191951 A1* | 8/2007 | Branch ............ 623/17.11 |
| 2008/0119853 A1 | 5/2008 | Felt |
| 2008/0133017 A1* | 6/2008 | Beyar ............ A61F 2/4425 623/17.16 |
| 2008/0140206 A1* | 6/2008 | Felt ............ A61F 2/4611 623/17.16 |
| 2008/0154379 A1 | 6/2008 | Steiner |
| 2008/0234822 A1 | 9/2008 | Govil |
| 2009/0157186 A1 | 6/2009 | Magerl |
| 2010/0256680 A1 | 10/2010 | Pasquet |
| 2010/0268349 A1 | 10/2010 | Bianchi |
| 2010/0305704 A1 | 12/2010 | Messerli |
| 2011/0320000 A1* | 12/2011 | O'Neil ............ A61B 17/1659 623/17.16 |

* cited by examiner

SPINAL FUSION IMPLANTS AND RELATED METHODS

CROSS REFERENCE TO RELATED APPLICATIONS

This application claims the benefit of the filing date of U.S. Provisional Application No. 61/554,875, which was filed on Nov. 2, 2011. The contents of U.S. Application No. 61/554,875 are incorporated by reference in their entirety as a part of this application.

BACKGROUND

The present application relates to spinal fusion surgery, and more particularly, to a system for promoting fusion across an intervertebral disc space.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The system of spinal fusion implants disclosed herein boasts a variety of inventive features and components that warrant patent protection, both individually and in combination.

Figure 1:
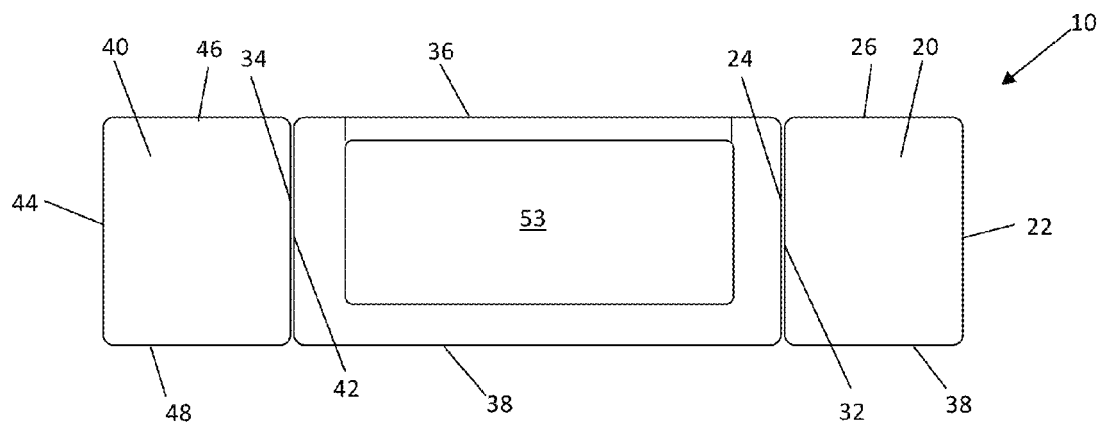
FIG. 1 is a top view of the system of spinal fusion implants according to an exemplary embodiment.
Figure 2:
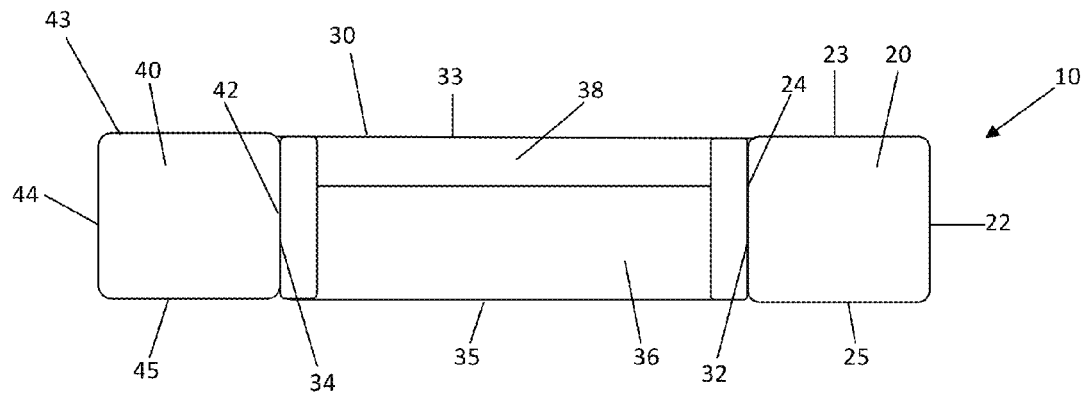
FIG. 2 is an anterior view of the system of spinal fusion implants according to the exemplary embodiment of FIG. 1.
Figure 3:
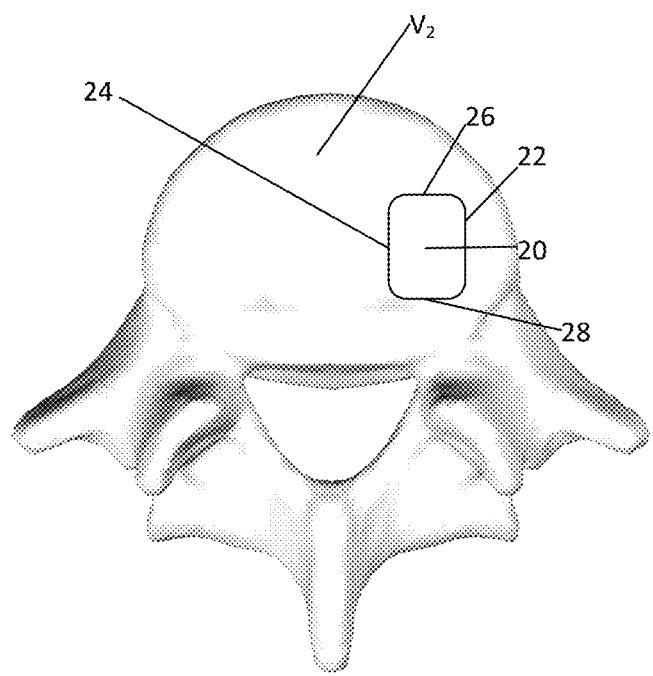
FIGS. 3-6 illustrate a method of inserting the system of spinal fusion implants into the intervertebral disc space.
Figure 4:
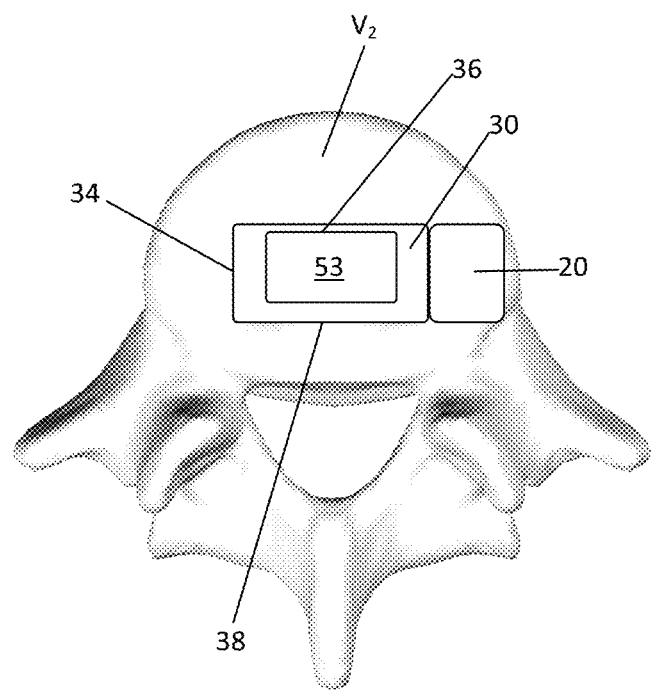
Figure 5:
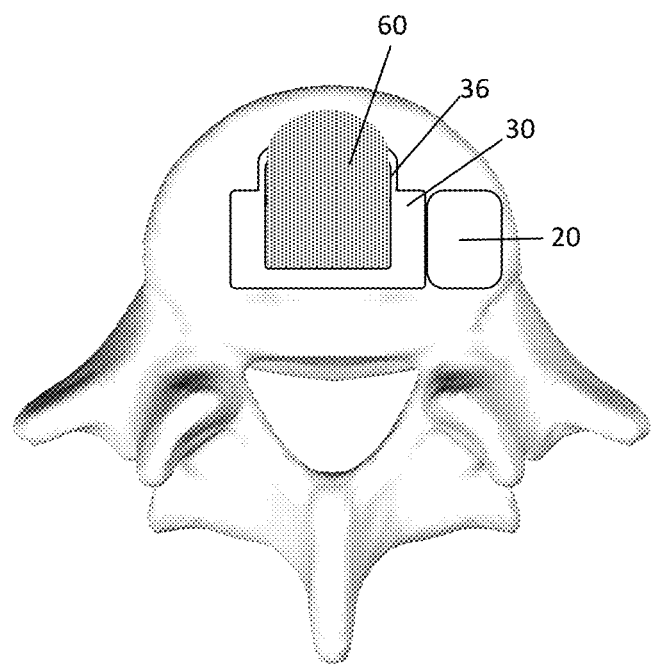
Figure 6:
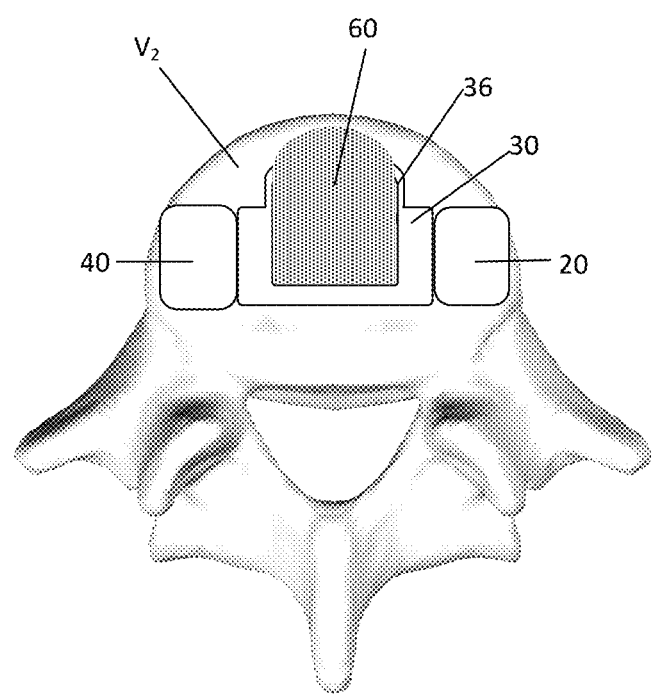

FIGS. 1-6 illustrate a system of spinal fusion implants for promoting fusion across an intervertebral disc space according to an exemplary embodiment. The system 10 includes a first intervertebral implant 20, a second intervertebral implant 30 and a third intervertebral implant 40, dimensioned for insertion into an intervertebral disc space via a lateral approach. The first implant 20, second implant 30 and third implant 40 are constructed of any suitable biocompatible material. According to an exemplary embodiment, the implants 20, 30, 40 are constructed primarily of radiolucent material and comprise radiopaque markers to aid in the positioning of the implants during surgery and/or visualization of the implants in postoperative imaging. Each of the implants 20, 30, 40 may also be equipped with anti-migration features on the top 23, 33, 43 and/or bottom surfaces 25, 35, 45.

The first intervertebral implant 20, also referred to as the distal implant 20, has a first bone contacting or top surface 23, a second bone contacting or bottom surface 25, a leading end wall 22, a trailing end wall 24, and anterior wall 26 and a posterior wall 38. The first implant 20 has a length extending between the leading end wall 22 to the trailing end wall 24, a height extending from the top surface 23 to the bottom surface 25, a width extending between the anterior wall 26 and the posterior wall 28.

The second intervertebral implant 30, also referred to as the medial implant 30, has a first bone contacting or top surface 33, a second bone contacting or bottom surface 35, a leading end wall 32, a trailing end wall 34, a flexible anterior wall 36 and a rigid posterior wall 38. The flexible anterior wall 36 may be constructed of any flexible biocompatible material capable of being deformed when a force is applied to the anterior wall 36. The second intervertebral implant 30 further comprises a fusion aperture 53 extending therethrough from the top surface 33, through the bottom surface 35. The second implant 30 has a length extending between the leading end wall 32 to the trailing end wall 34, an anterior height extending from the top surface 33 to the bottom surface 35 at the anterior wall 36 and a posterior height extending from the top surface 33 to the bottom surface 35 at the posterior wall 38, and a width extending between the anterior wall 36 and the posterior wall 38. According to one exemplary embodiment, the posterior height of the second implant 30 is greater than the anterior height.

The third intervertebral implant 40, also referred to herein as the proximal implant 40, has a first bone contacting or top surface 43, a second bone contacting or bottom surface 45, a leading end wall 42, a trailing end wall 44, and anterior wall 46 and a posterior wall 48. The third implant 40 has a length extending between the leading end wall 42 to the trailing end wall 44, a height extending from the top surface 43 to the bottom surface 45, a width extending between the anterior wall 46 and the posterior wall 48.

The proximal implant 40 and distal implant 20 are dimensioned for placement adjacent the medial implant 30 on the proximal and distal lateral aspects, respectively, of the inferior vertebral body $V_2$ adjacent an intervertebral disc space. Although not shown, an alternate embodiment wherein the proximal implant 40 and distal implant 20 each further includes a fusion aperture extending from the top surface 43, 23 through the bottom surface 45, 25 is also contemplated. According to one exemplary embodiment, such as the one shown in FIGS. 1-6, the proximal implant 40 and distal implant 20 are substantially identical in size and shape. According to an alternate embodiment, the proximal implant 40 has a greater length, height and/or width dimension than the distal implant 20 or vice versa. According to another alternative embodiment, the top 43, 23 and/or bottom surfaces 45, 25 may be angled from the anterior wall 46, 26 to the posterior wall 48, 28 to create lordosis or kyphosis at the treated vertebral level.

According to an alternative embodiment, the medial implant 30 is dimensioned to be implanted in the intervertebral disc space alone, i.e. without the distal implant 20 and proximal implant 40. According to this alternative embodiment, the implant 30 has a length between the leading end 32 and the trailing end 34 sufficient to span the intervertebral disc space, such that the leading end wall 32 rests on the distal lateral aspect of the inferior vertebral body $V_2$ and the trailing end walk 34 rests on the proximal lateral aspect of the inferior vertebral body $V_2$. According to one aspect, at least a portion of the anterior wall 36 may be constructed of flexible material. According to another aspect, at least a portion of the anterior wall 36 has a height that is less than the height of the posterior wall 38 to allow bone growth promoting material to overflow the fusion aperture 53 and spill into the intervertebral disc space anterior to the implant 30.

FIGS. 3-6 illustrated a method of inserting the system of implants 10 into an intervertebral disc space. According to the exemplary method, the disc space to be treated is accessed via a lateral approach, and the disc space is prepared for implant insertion according to known techniques. Once the disc space has been prepared, the first implant 20 is inserted into the disc space and placed in a desired location on the distal lateral aspect of the disc space (as shown, for example, in FIG. 3). After the distal implant 20 has been placed, the second intervertebral implant 30 is advanced into the disc space and positioned adjacent the distal implant 20, as shown, for example in FIG. 4. Before or after the medial implant 30 has been placed in the desired position within the disc space, the fusion aperture 53 of the medial implant may be packed with a bone growth enhancing material 60. The bone growth enhancing material may be autograft, allograft, growth factors, a synthetic bone graft or a combination thereof. According to one exemplary embodiment, the fusion aperture 53 is packed with an amount of bone growth enhancing material sufficient to deform the flexible anterior wall 36 of the medial implant, cause the flexible anterior wall 36 to be displaced anteriorly. According to an alternative embodiment, the fusion aperture 53 is overpacked with bone growth enhancing material 60 until the bone growth enhancing material overflows into the disc space anterior to the system of implants 10. After the medial implant 30 is placed in the desired position within the intervertebral disc space, and packed with the desired amount bone growth enhancing material, the proximal implant 40 is inserted into the disc space and positioned adjacent the medial implant 30, as shown, for example, in FIG. 6.

According to another exemplary embodiment, the first 20, second 30 and third 40 implants may have insertion tool apertures for receiving an insertion tool therethrough in each of the leading end walls 22, 32, 42 and trailing end walls 24, 34, 44. For example, the distal implant 20 may be coupled to a first inserted and inserted and placed in a desired position. The medial implant 30 is coupled to a second inserter, the second inserter being cannulated and having a hollow interior dimension that is greater than the exterior dimension of the first inserter, such that the second implant and inserter can be inserted over the first inserter, with the first inserter being received through the insertion tool apertures in the leading end wall 32 and the trailing end wall 34 of the medial implant 30. Finally, the proximal implant 40 is coupled to a third inserter, wherein the third inserter is cannulated and has a hollow interior dimension that is greater than the exterior dimension of the second inserter, such that the third inserter coupled to the proximal implant 40 can be inserted over the second inserter, with the second inserter being received through the leading end aperture 42 and the trailing end aperture 44 of the proximal implant 40.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A method for promoting fusion across an intervertebral disc space, the method comprising the steps of:
   accessing an intervertebral disc space via a lateral approach;
   inserting a first implant having a top surface, a bottom surface, a leading end wall, a trailing end wall, an anterior wall and a posterior wall;
   positioning said first implant such that the leading end wall rests on a distal lateral aspect of an inferior vertebral body adjacent the intervertebral disc space;
   inserting a second implant having a top surface, a bottom surface, a leading end wall, a trailing end wall, a flexible anterior wall and a rigid posterior wall, said leading end wall, trailing end wall, flexible anterior wall and rigid posterior wall defining a fusion aperture;
   positioning said second implant such that the leading end wall of the second implant runs along a length of and adjacent to the trailing end wall of the first implant;
   packing the fusion aperture of the second implant with bone growth enhancing material after the second implant is positioned within the intervertebral disc space;
   inserting a third implant having a top surface, a bottom surface, a leading end wall, a trailing end wall, an anterior wall and a posterior wall after the fusion aperture of the second implant has been packed with bone growth enhancing material; and
   positioning the third implant such that the leading end of the third implant runs along a length of and adjacent to the trailing end wall of the second implant, and the trailing end of the third implant rests on a proximal lateral aspect of the inferior vertebral body.

2. The method of claim 1, wherein the amount of bone growth enhancing material packed into the fusion aperture is sufficient to deform the flexible anterior wall of the second implant in an anterior direction.

3. The method of claim 1, wherein the first implant has a first length, the second implant has a second length, and the third implant has a third length and wherein said second length is greater than said first length and said third length.

4. The method of claim 3, wherein the length of the first implant is equal to the length of the third implant.

5. The method of claim 1, wherein said rigid posterior wall of said second implant has a height that is greater than a height of the flexible anterior wall of the second implant.

6. The method of claim 1, wherein the first implant and the second implant are identical in shape.

* * * * *